United States Patent [19]

Plester et al.

[11] Patent Number: 4,830,192

[45] Date of Patent: May 16, 1989

[54] METHODS OF DISCRIMINATING BETWEEN CONTAMINATED AND UNCONTAMINATED CONTAINERS

[75] Inventors: George Plester, Essen, Fed. Rep. of Germany; Warren E. Leddon; David E. Dalsis, both of Marietta, Ga.

[73] Assignee: The Coca-Cola Company, Atlanta, Ga.

[21] Appl. No.: 76,735

[22] Filed: Jul. 23, 1987

Related U.S. Application Data

[63] Continuation-in-part of Ser. No. 892,983, Aug. 4, 1986.

[51] Int. Cl.<sup>4</sup> .................. B07C 5/02; B07C 5/342; G01N 21/90; G01N 35/06
[52] U.S. Cl. ...................... 209/3.1; 73/61.1 R; 73/863.91; 209/523; 209/564; 209/577; 209/580
[58] Field of Search .................. 209/3.1–3.3, 209/509, 522–524, 538, 546, 549, 552, 555, 556, 558, 563–567, 570, 571, 576–579, 587–589; 73/53, 61.1 R, 863, 863.91, 864.81, 864.91; 250/223.2, 565, 341; 356/36, 240, 426, 427, 440; 422/64

[56] References Cited

U.S. PATENT DOCUMENTS

| | | | |
|---|---|---|---|
| 2,593,311 | 4/1952 | Johnson et al. | 209/524 X |
| 2,735,017 | 2/1956 | Beard et al. | 209/524 X |
| 3,266,292 | 8/1966 | Bailey | 73/863.91 X |
| 3,417,241 | 12/1968 | Davis | 209/3.1 |
| 3,712,116 | 1/1973 | Andre | 73/61.1 R X |
| 3,802,782 | 7/1974 | Natelson | 250/565 X |
| 4,055,252 | 10/1977 | Klamm et al. | 209/566 X |
| 4,121,103 | 10/1978 | Calhoun | 250/343 |
| 4,227,886 | 10/1980 | Bullock et al. | 356/240 X |
| 4,551,627 | 11/1985 | Reich | 250/223 B X |

FOREIGN PATENT DOCUMENTS

| | | | |
|---|---|---|---|
| 2944434 | 5/1981 | Fed. Rep. of Germany | 209/522 |
| 3245908 | 6/1984 | Fed. Rep. of Germany | 209/522 |
| 53-133085 | 11/1978 | Japan | 356/240 |
| 55-36733 | 3/1980 | Japan | 356/240 |

Primary Examiner—Robert B. Reeves
Assistant Examiner—Edward M. Wacyra
Attorney, Agent, or Firm—Birch, Stewart, Kolasch & Birch

[57] ABSTRACT

Methods of discriminating between contaminated and uncontaminated containers prior to washing is disclosed characterized by the testing of the residue of the container to determine if the residue is residue of the original product packed in the container. If the residue is not sufficiently similar to the original product, the container is rejected as contaminated.

6 Claims, 3 Drawing Sheets

METHODS OF DISCRIMINATING BETWEEN CONTAMINATED AND UNCONTAMINATED CONTAINERS

CROSS REFERENCE TO RELATED APPLICATIONS

This is a continuation-in-part of application Ser. No. 892,983, filed Aug. 4, 1986.

BACKGROUND OF THE INVENTION

This invention relates generally to container inspection systems, such as glass and plastic containers for the presence of contaminants and hazardous materials. More specifically, this invention relates to a method of identifying uncontaminated containers by detecting the residue of the product originally packaged in the container.

In many industries, including the beverage industry, products are packaged in containers which are returned after use, washed and refilled. Typically refillable containers are made of glass which can be easily cleaned. These containers are washed and then inspected for the presence of foreign matter.

Glass containers have the disadvantages of being fragile and, in the larger volumes, of being relatively heavy. Accordingly, it is highly desirable to use plastic containers because they are less fragile and lighter than glass containers of the same volume. However, plastic materials tend to absorb a variety of organic compounds which may later be desorbed into the product thereby adversely affecting the quality of the product packed in the container. It has been found that the existing methods of inspection are inadequate to detect containers which may have absorbed contaminants.

SUMMARY OF THE PRIOR ART

Two kinds of foreign matter detecting devices, one for inspecting the body (barrel) of a bottle and the other for inspecting the bottom, are known in the art. In the former device, light is externally applied to the bottle while the bottle is being rotated, and light passed through the bottle is detected by a photoelectric element. The photoelectric element is employed to compare the quantity of transmission light obtained when a certain region of the bottle has a foreign matter to the quantity of transmission light obtained when the certain region has no foreign matter. Typically the entire body of the bottle is inspected for a foreign matter. Illustrative of the above described detection system are the devices described in U.S. Pat. No. 4,376,951 (Mar. 15, 1983, Miyazawa) which comprises a photoelectric conversion device having a number of light receiving elements; and a video signal processing device for successively subjecting to comparison and discrimination the detection signals of variable two adjacent points which are detected by the photoelectric conversion device, to determine whether or not the bottle has a foreign matter.

Detecting devices which measure the degree of transmission through a container have the disadvantage that they cannot detect the presence of many contaminants that may have been absorbed into the wall of the container because some contaminants do not affect the transmission of light through the container.

U.S. Pat. No. 4,551,627 (Nov. 5, 1985 Reich) discloses apparatus for inspecting residual liquid such as water, oil, and liquid soap in refillable beverage containers. The apparatus is intended to detect liquids such as oil, and liquid soap which may contaminate the containers. In the apparatus disclosed small quantities of liquid contaminant are detected and the containers containing such residues are removed from the refillable container process line. The method for detecting the contaminant comprises the steps of: measuring optical transmittances of a combination of the contaminant to be detected and a container wall in which the contaminant is accommodated; selecting two optical pass-bands, one of which is relatively high transmittance level with respect to the contaminant to be detected while the other of which is relatively low transmittance level with respect to the contaminant to be detected; measuring light quantities at the two optical pass-bands when light passes through the bottom and neck of the container; converting the light quantities into respective two electric signals; and comparing one electric signal with respect to one pass-band with the other electric signal with respect to the other pass-band. While the apparatus described by Reich may be suitable to detect one or two predetermined liquid contaminants which may remain in the container, its utility is limited in situations where the possible contaminants are numerous, or the contaminant has been absorbed by the wall of the container. Additionally, the apparatus depends on the transmittance of the contaminant to be detected, and that physical property varies widely depending on the contaminants. This device is typically used to inspect washed glass packages for residual diluted caustic solutions, and not unwashed packages as per the present invention.

U.S. Pat. No. 4,221,961 (Sep. 9, 1980, Peyton) discloses an electro-optic bottle inspector. The device is constructed so that it can detect particles or liquid in a bottle. It has a light source to be disposed under the bottle bottom, a rotative scanner head to be disposed over the bottle neck to receive light passing through the bottle bottom from the light source, and a detector for receiving light reflected by the surface of the scanner head to detect only particulate matters on the bottle bottom. The scanner has reflecting segments and non reflecting portions. The reflecting segments reflect the light passing through the bottle bottom so as to focus a bottle bottom image onto the detector. If there are particulate matters on the bottle bottom, they block the light from the light source to cause a dip in detector output. The non-reflecting portions are provided with an infrared detector for detecting the infrared radiation passing through the bottle bottom. The light to be received by the infrared detector is filtered so that only light having wavelengths in or near one of the absorption bands of liquid to be detected can pass through to reach the infrared detector. If there is liquid in the bottle bottom, the light is partially absorbed to cause a dip in A.C. coupled amplitude of the infrared detector providing an indication of the presence of the liquid. This device is typically used to inspect washed glass returnable bottles for foreign materials that may adhere to the inside of the bottle and could not be removed by the washing device.

U.S. Pat. No. 4,087,184 (May 2, 1978, Knapp, et al.) discloses a method and apparatus for inspecting liquids in transparent containers. The method comprises the steps of illuminating the liquid with a constant intensity light source, imaging the entire illuminated liquid volume, including the meniscus, into a plurality of image planes with fiber optic bundles, and monitoring the fiber optic bundles with an array of constant sensitivity photo transducers. Each photo transducer continually translates the illumination value of the vial image of an assigned and separate unit volume of the liquid-filled container into a voltage signal and each signal is monitored for a signal change indicative of particulate movement. The interfering output signal due to the meniscus decay is corrected, and the accept/reject decision is based upon a composite signal representative of all the differentiated signals received from the array of photo transducers.

U.S. Pat. No. 4,083,691 (Apr. 11, 1978, McCormack, et al.) discloses a method for detecting contaminants in water. The method rapidly detects organic pollutants in water utilizing chemical effervescence to accelerate release of contaminants into the atmosphere above the water sample where they can be detected by conventional air pollution detector tubes. An apparatus for detecting contaminants in the atmosphere above the water solution by detector tube is also disclosed.

U.S. Pat. No. 3,966,332 (Jun. 29, 1976, Knapp et al.) discloses a method and apparatus for inspecting liquids in transparent containers. The apparatus automatically inspects liquid filled containers for particulate contaminants by relative size. The method comprises the steps of illuminating the liquid with a constant intensity light source, dissecting the image of the entire illuminated liquid volume, including the meniscus, with fiber optic bundles and monitoring the fiber optic bundles with an array of constant sensitivity photo sensors. Each photo sensor continually translates the illumination value of an assigned and separate cross sectional unit area of the vial image into a voltage signal and monitors each signal for a signal change indicative of particulate movement. The interfering output signal due to the meniscus decay is corrected, and the accept/reject decision is based upon a composite signal representative of all the differentiated signals received from the array of photo sensors.

U.S. Pat. No. 4,459,023 (July 10, 1984, Reich, et al.) discloses an electro-optic inspection system for transparent or semitransparent containers. The electro-optic inspection system disclosed uses a polarized, scanned optical beam and an array of polaroid optical detectors and a logic signal processing system thereby to securely detect the defects on the transparent or semitransparent containers.

All of the devices describe heretofore have the disadvantage that they depend upon either the presence of particles having a size of at least 5 mm. or the detection of a physical property of a specific liquid contaminant as a means of indicating possible contamination. In the case of contaminated plastic bottles the presence of contaminants may not be manifested with the presence of particles of that size or of any measurable amount of liquid. Rather the contamination would be diffused in the wall of the container and undetectable using the optical methods described in the references. Another difficulty encountered in the possible contamination of plastic containers is that the possible contaminants are numerous and the physical and chemical properties of the contaminants are diverse. Accordingly, a system that is capable of detecting a contaminant such as insecticide may not detect herbicides or fuel.

Accordingly, a first object of this invention is to enable the discrimination between containers that may have been contaminated from bottles that have not been contaminated.

A second object of the invention is to provide a novel system simple in construction and low in manufacturing cost, which can readily detect containers likely to be free of contaminants with high accuracy, thus contributing to labor saving in inspecting bottles.

A third object of the invention is to provide a novel system which can operate to distinguish between plastic containers which may have different contaminants absorbed in the walls of the container from containers which contain residue of the original product.

A fourth object of the invention is to provide a system for identifying containers having a residue of the original product packed in the container by detecting the presence of the residue.

A fifth object of the invention is to provide a system for identifying containers having a residue of the original product packed in the container by detecting the presence of a component of the residue.

SUMMARY OF THE INVENTION

These and other objects of the invention are accomplished by the present invention by means of a method and apparatus for discriminating between a contaminated and uncontaminated bottle in which various physical parameters of the residue of the bottle are compared to the physical parameters of the product originally packed in the container. If the physical parameters of the residue correlate to the parameters of the product originally packed in the container, the bottle containing said residue is sent to the standard washer of the bottling facility. If the physical parameters of the residue do not correlate to the parameters of the product originally packed in the container, the bottle containing said residue is subjected to further inspection, or subjected to a special contaminant extraction process or discarded.

The novel features of this invention are set forth in the appended claims. The nature, principle and utility of the invention will become more apparent from the following detailed description when read in conjunction with the accompanying drawings, in which like parts are designated by like reference numerals.

DETAILED DESCRIPTION OF THE INVENTION.

To fully understand the present invention it is important to understand the differences between the physical performance of resinous materials (e.g. polyethylene, PET, acrylonitrile styrene copolymers, polycarbonates and the like) and glass. Glass is impervious to penetration by most substances. Unlike glass, contaminants can migrate into the walls of a container which is made of resinous materials. Contaminants that migrate into the walls of the containers may be desorbed into the product if the container is refilled. Many contaminants, even at minute concentrations will adversely affect the taste or aroma of a consumable material. A very large number of contaminant types and concentrations may exist in the containers. Existing detection methods cannot characterize residues fast enough for practical applications. The migration of some contaminants into the walls of the containers may not result in physical characteristics which are visually detectable. Accordingly, the existing detection systems are inadequate to detect such contamination.

Figure 1:
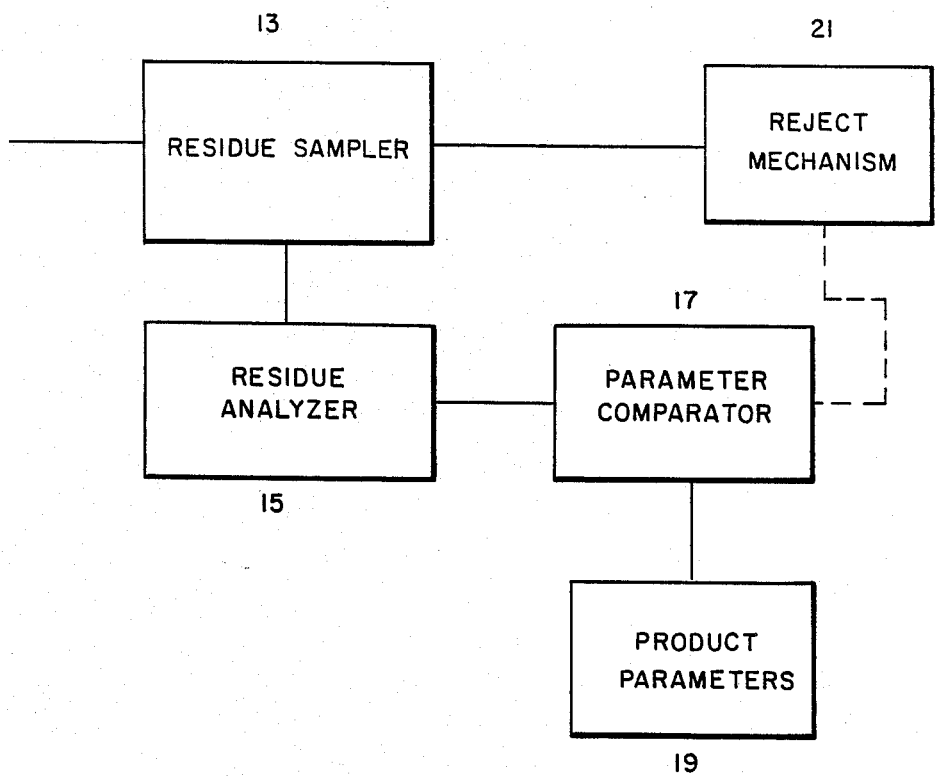
FIG. 1 is a schematic diagram of a system incorporating the method of discriminating between contaminated and uncontaminated containers according to the present invention.

Shown in FIG. 1 is a simplified schematic of a system 11 for discriminating between contaminated bottles and uncontaminated bottles. Bottles returned from the trade are transported to a residue sampler 13 where samples of residue from the bottle are obtained. Samples of the residue are taken to a residue analyzer 15 which measure a physical response of the residue sample. A sample signal corresponding to the physical response from the sample is sent to a parameter comparator 17 which compares the sample signal to corresponding values for the product originally packed in the container which are stored in a memory 19. The parameter comparator 17 sends a reject signal to a reject mechanism 21 if the sample signal does not correlate to the stored product parameters. The reject mechanism 21 diverts the bottles in response to the reject signal.

Figure 2:
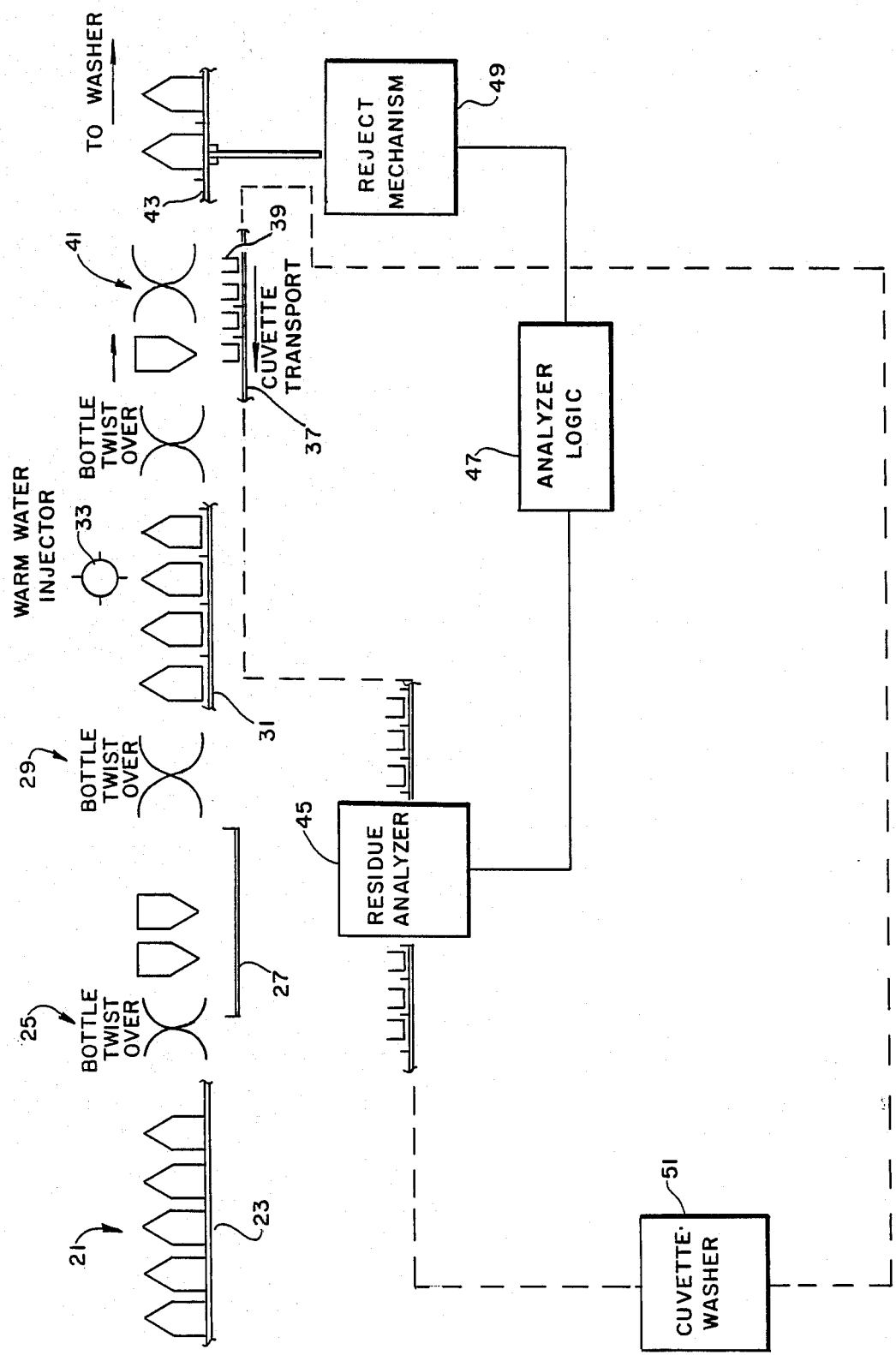
FIG. 2 is a more detailed schematic of one embodiment of the present invention.

In FIG. 2 there is presented a more detailed schematic of the system 11 incorporating the method of discriminating between contaminated and uncontaminated containers according to the present invention. Bottles 21 returned from the trade are loaded on an initial conveyor system 23 in a bottling plant to be washed and refilled. The bottles are transported to a first twist over station 25 where the bottles are turned upside down to remove any large remnants. The large remnants are dropped onto a refuse receptacle 27 and discarded. The bottles are then conveyed to a second twist over station 29 where they are reoriented with the open neck portion disposed upwardly and are placed on a discrete receptacle conveying mechanism 31. The conveying mechanism 31 may be a standard pocket chain type conveyer system. The bottles are then transported to a position below a water injector 33 where a specified volume of distilled water is injected into the bottles. The bottles proceed to a third bottle twist over station 35. Disposed below the third twist over station 35 is a cuvette transport system 37 comprising a plurality of glass cuvettes 39 disposed on a conveyer system discrete and identified positions for each cuvette. The bottles are then transported to a fourth twist over station 41 and placed on a conveyer system 43. Each position of a bottle on the conveyer system 43 corresponds to a position of a cuvette 39 on the cuvette transport system 37.

The cuvettes 39 containing samples of the dilute residue are transported to a residue analyzer 45. The residue analyzer 45 measures one or more physical characteristics of the dilute residue and provides an input to the analyzer logic system 47. The analyzer logic system 47 compares the readings of the physical characteristics with the characteristics of the product that was originally packed in the container. If the physical characteristics of the dilute residue do not correlate to the physical characteristics of the original product within the limits established for the specific characteristics, then the bottom from which the residue was obtained is considered contaminated and a reject signal is generated by the analyzer logic system 47. The reject signal is received by the logic system of a reject mechanism 49 which diverts the contaminated bottle from the conveyer system 43. The contaminated bottle may be discarded or conveyed to a a second inspection station or a contaminant extraction station (not shown).

After the cuvettes 39 are processed through the residues analyzer 45 they are transported to a cuvette washer 51 where they are thoroughly washed to remove all residues from the cuvettes. The cuvettes 39 are then recycled through the cuvette transport system 37.

Figure 3:
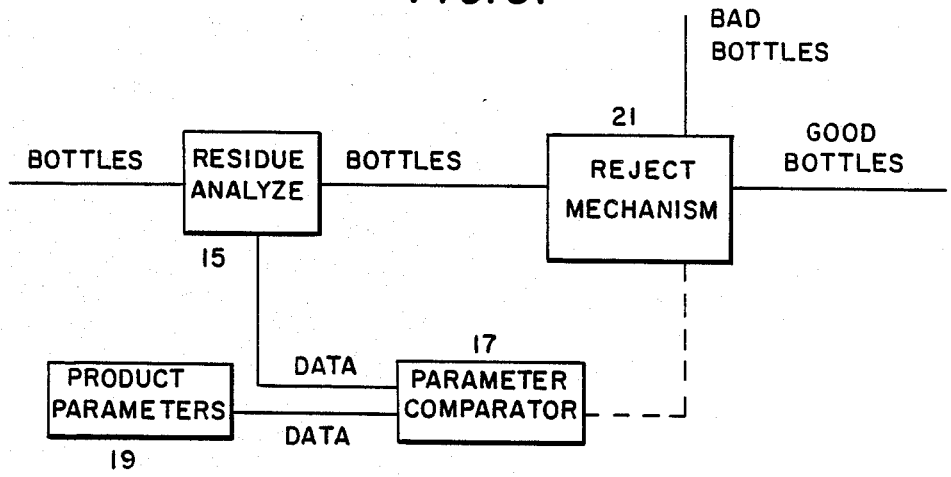
FIG. 3 is a schematic diagram of an alternate system according to this invention.

Shown in FIG. 3 is a simplified schematic of system 12 which has the same purpose and the same components as system 11 except that residue sampler 13 is not required. Residues are measured in the residue analyzer 15 without being removed from the original container. The measurements of physical response are those that can be made in the original container and are nondestructive to the container. The other parts of system 12 function as those in system 11.

Figure 4:
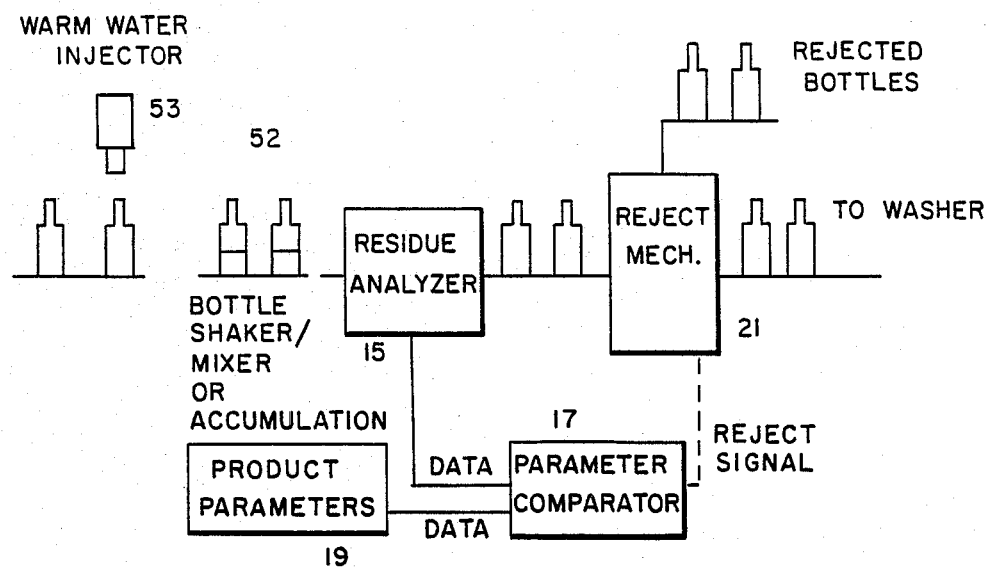
FIG. 4 is a schematic diagram of an alternate system according to this invention.

FIG. 4 illustrates how the residue analysis can be conducted in the container being analyzed. Bottles are transported in a conveyor system and are sequentially disposed under a water injector 33 (like that described in FIG. 2) if the analyzer requires a liquid for analysis. Warm water from the water injector 33 is injected in each bottle sufficient to dissolve the required amount of residue and provide sufficient volume for the analyzer. The bottles with the warm water are then accumulated or transported to a bottle shaker/mixer 54 to thoroughly dissolve the residue to the required concentration. The bottle with the residue is then transported to a residue analyzer 15 like that described in FIG. 3. The rest of the system operates like the system in FIG. 3.

Product Residue Analyzers

Numerous techniques, or a combination thereof, can be utilized to identify the residue of a container as the product originally packed in the container. Typically these techniques will detect a characteristic of the product or an ingredient of the product which can be used to discriminate the product from a contaminant. Below are descriptions of various techniques which can be incorporated in the residue analyzers 15 utilized in the method of the present invention.

A. Direct Methods of Detection.

Substances can be characterized by measuring the quantity and quality of electromagnetic radiation emitted, reflected, transmitted, or diffracted by the sample. The various methods utilized for analysis of chemical compositions using electromagnetic radiation are summarized below.

1. Emission Spectroscopy.

Emission spectroscopy is used to determine the structure of compounds from the wavelength configuration of their emission spectra. The sample is generally thermally excited in an arc until it emits its characteristic radiation. A detector is used to measure the relative amounts of radiation at the characteristic wavelengths. Although typically used for solids and metal analysis this analytical tool can be used to characterize liquids.

2. Multiparameter Luminescence Analysis.

Many substances when subjected to electromagnetic excitation tend to emit radiation at characteristic wavelengths. The amounts and spectra of the emitted radiation are related to the molecular structure of the sample. A multichannel fluorimeter can be used to collect luminescence intensity, excitation, and emitted wavelength data from unknown container residues. This dimensional signature can be compared to, using computerized pattern recognition, to a reference signature for uncontaminated residues.

3. Infrared Spectrophotometry.

The frequency and amounts of infrared radiation that a sample absorbs is characterized by the molecular structure of the various species in the sample. For organic compounds the infrared spectrum is highly characteristic and in effect provides a fingerprint of the compounds.

4. Near Infrared Spectrophotometry

This technology is similar to that of infrared spectrophotometry, described above, except that monochromatic light in the near infrared region (1,100 nanometers to 2,500 nanometers) is directed to the unknown sample. The near infrared spectrum produces many overlapping overtones of the infrared spectrum. These overtones can be analyzed with the assistance of computerized multi-linear regression analysis to yield a more defined sample identification.

5. Ultraviolet/Visible (Colorimetric Absorption Spectroscopy.

The concentration of an ultraviolet (UV) or visible light absorbing material in a mixture can be readily measured. With a UV/visible spectrophotometer the absorbing components of the sample can be characterized by their absorption versus wavelength patterns (spectral signature). A reference spectral signature can be generated for product residues. Computerized pattern recognition techniques can be used to classify the residue as contaminant or product. These determinations can be accomplished with available colorimeters which determine the degree of absorption of rays of light of predetermined and characteristic wavelengths to establish the specific colors of a sample or sample solution. UV/visible refers to light in the range of 300 to 700 nanometers. Visible light is generated from a white light source and UV light is generated from an UV light source.

More specifically, the spectral signature can be determined by choosing identification wavelength ranges for product utilizing light filters. In selecting identification wavelength ranges at least one discrete, preselected identification wavelength range is necessary and three to eight discrete, preselected identification wavelength ranges may be preferred depending upon the spectral signature of the actual product. This specific color information can then be utilized to classify the sample and reject a contaminated container in a product filling line application. The system utilizing this technology is shown in FIG. 4. Colorimetric absorption spectroscopy is one of the preferred embodiments of the invention.

6. Raman Spectroscopy.

Raman spectroscopy is based upon the shift in wavelength of monochromatic light scattered by a sample. The shift in wavelength is indicative of the molecular structure of the sample. In some cases the Raman spectrum duplicate that of the infrared spectrum, but in many cases additional information can be obtained. This technology could be used in tandem with Infrared Spectrophotometry to provide a more effective residue discrimination.

7. Other Light Measurements.

The molecular structure of the components of a sample can also be characterized by the effect that the structure has on light transmitted through the sample. Among the physical effects that can be measured are:
refractive index of the sample solution;
light scattering of suspensions;
optical rotation of polarized light and
refractive index of the sample;
turbidity of the sample;
density of the sample.

All of the physical effects described above can be detected by photodetectors which are commercially available. The specific method to be employed will depend on the product originally packed in the container, or the component of the product which will be keyed. Preferably more than one method can be used in order to raise the reliability of the residue detector.

Of particular interest in application in plastic containers for soft drinks is differential light scattering. U.S. Pat. No. 4,548,500 (Oct. 22, 1985, Wyatt) discloses a process and apparatus for identifying or characterizing small particles based upon the measurement of certain optical observables produced as each particle passes through a beam of light, or other electromagnetic radiation. A highly coherent beam of, preferably, monochromatic vertically polarized light passes through a spherical array of detectors, or receptors with fiber optics means to transmit incident light to a set of detector is employed. The sample containing the small particles intersects the beam at the center of the spherical array. Selected observables calculated from the detected scattered radiation are then used to recall specific maps, from a computer.

The foregoing principle was adapted in U.S. Pat. No. 4,490,042 (Dec. 25, 1984, Wyatt) to determine the properties of wine by illuminating an aliquot or a dilution thereof with a beam of monochromatic light, measuring the light scattering pattern produced, comparing this pattern to that of a reference pattern, and using the difference between the two patterns as the quantitative measure. A variation of the method is disclosed wherein a number of measurements at a selected set of angles over a period of time are measured and, at each selected angle, the intensity is measured several times. In this method, the average of the intensities so detected at each selected angle is determined, and the numerical set of the averages and the fluctuation of each detected value from the average is used to characterize the beverage.

The foregoing principle can be utilized in the method of the present invention to characterize the product and compare it to the residue. In another of the preferred embodiments of the invention, an aliquot of residue is diluted with filtered deionized water, placed in a cuvette, and illuminated diametrically by means of a vertically polarized fine laser beam. An array of detectors, or a rotating single detector, measures the scattered light intensity as a function of scattering angle, generally the plane of the laser. Also polarizing filters are utilized to read the scattered light in a plane perpendicular to the plane of polarization of the laser. This scattering variation is then recorded digitally, and compared with a stored library of such scattering patterns for the original product contained in the bottle. If the diluted residue readings are not substantially similar to the stored readings for the original product the residue is considered a contaminant. The contaminated container may then be treated with special solvents to extract possible contaminants, or may be discarded.

8. Flame Ionization Detectors.

The flame ionization detector consists of a small hydrogen flame burning in an excess of air which is surrounded by an electrostatic field. Organic compounds injected into the flame are burned. During the combustion, ionic fragments are collected, producing an electric current proportional to the number of carbon atoms in the sample. This phenomenon allows for sample identification.

9. X-Ray fluorescence.

X-Ray fluorescence involves the excitation of a sample by irradiation of the material with intense short wavelength x-rays. The x-rays subsequently emitted from an excited element have a wavelength characteristic of that element and an intensity proportional to the number of excited atoms.

10. Laser-Induced Breakdown Spectroscopy. (LIBS)

LIBS uses a commercial laser to deliver pulses of light lasting less than a microsecond. The intense light, which is focused on a tiny area of the sample reduces the material to its elemental constituents. The resulting plasma is analyzed by atomic emission spectroscopy.

11. Electrical Conductivity.

A simple apparatus may be used to measure the electrical conductivity of a sample of the residue.

12. Gas Chromatography.

Gas chromatography technology utilizing an appropriate detector can be used to analyze residue of product residue and/or microorganisms including mold and yeast indicating the presence of product.

13. Mass Spectroscopy.

In the mass spectrometer, molecules are bombarded with a beam of energized electrons. The molecules are ionized and broken up into many fragments, some of which are positive ions. Each kind of ion has a particular ratio of mass to charge. The ions are separated according to their mass using one of a number of available techniques, such as by a uniform magnetic field. The charge of each ion species is measured by measuring the current induced on an electrode. In general each molecular structure generates a unique mass spectrum. Detection of uncontaminated residues can be accomplished by tuning a mass spectrum leak detector to a unique residue constituent. Peak response indicates an uncontaminated residue.

14. Nuclear Magnetic Resonance. (NMR)

The nuclei of atoms are considered to be spinning charged particles. The spinning of a charged particle generates a magnetic moment aligned with the axis of the spin. If a substance is irradiated with radiation of constant frequency, in a magnetic field of varying strength, then at some value of the field strength absorption occurs and a signal is observed. A typical absorption spectrum for will show many absorption peaks indicating the molecular structure of the compound. Micro- processor controlled NMR spectrometers collect the spectrum data for computer analysis.

B. Detection of Reaction Products.

Basically the determination of chemical composition by the measurement of reaction products involves two steps. First, there is the promotion of the desired chemical reaction, and second there is the measurement of the reaction product as a means of determining the presence and quantity of a particular constituent in the product. The latter step may utilize some of the techniques outlined above. Typically the instruments used for measuring reaction products are:

Impregnated tape devices;
Photometric instruments (colorimeter and nephelometers);
Electrolytic conductance meters; and
Electrochemical devices.

Of particular interest in soft drink applications is the determination of sugar content in the residue. The analysis of test samples for the presence of sugars is common in many unrelated arts. For the most part these analyses can be characterized as oxidizing systems (indicators) which, when reduced, initiate reaction conditions leading to a detectable response, such as a color change or change in wavelength of ultraviolet light absorbed or reflected by the system. A family of indicator compounds known loosely in the art as "benzidine-type indicators" have also been developed. These benzidine-type indicators include benzidine, o-tolidine, 3,3',5,5'-tetramethylbenzidine, 2,7-diaminofluorene and the like. These compounds can undergo color changes in the presence of hydrogen peroxide and the enzyme peroxidase. In the glucose/glucose oxidase system glucose is oxidized to gluconic acid with the concomitant formation of $H_2O_2$. The formation of hydrogen peroxide which facilitates the subsequent, indicator related steps leading to observable color formation or other detectable response. To summarize the state of the art of sugar detection, sugar sensitive chemistries began to appear on the analytical scene as early as the middle of the 19th century with the advent of Fehling's solution and Tollens' reagent. Most of the "purely chemical" systems which have since emerged have been largely superseded by biochemical systems, particularly those which comprise a sugar oxidase, peroxidase and a peroxide-sensitive indicator of the benzidine type.

The sugar indications methods described above can be easily incorporated into a residue analyzer 15. The necessary oxidative reaction may be carried out in the bottle or container, or alternatively in the cuvettes 39 illustrated in FIG. 2.

A signal responsive to the color of the sugar indicator may be generated by a colorimeter such as that described in U.S. Pat. No. 4,519,710 (May 28, 1985 Luce, et. al.). Such a colorimeter comprises a source of optical radiation, a multichambered flow cell through which a solution to be monitored can flow, and photodetector devices responsive to radiation transmitted through the solution in the chambers of the flow cell. The radiation source may be monochromatic, or alternatively may emit radiation over a broad optical spectrum and be used in combination with discrete bandpass filters on the individual flow-cell chambers. The photodetector devices generate electrical outputs proportional to the intensity of the radiation transmitted through the solution. Electronic circuitry responsive to the outputs of the photodetector devices maintains the intensity of the radiation emitted by the radiation source at a substantially constant value.

In addition to sugar indicators, the methodology described above may be used with an appropriate pH indicator to characterize the residue by its pH.

The techniques describe above are characterized by the measurement of a physical response by the sample to be analyzed. All of the techniques have been embodied into commercially available devices. These devices measure the physical response of the sample to a give stimulus and convert that response into a form (usually digital) which can be processed by computers. While the numerous techniques have been described in the prior art none of these references nor any device or combination of components is like that of the present invention, either in arrangement or in the manner of its operation. While specific embodiments of the invention have been shown and described in detail to illustrate the application of the inventive principles, it will be understood that the invention may be embodied otherwise without departing from such principles.

Rejection Mechanisms

The reject mechanism 21 referred to in FIG. 1 may be a commercially available defective bottle rejection system such as described in U.S. Pat. No. 4,295,558 (Oct. 20, 1981 Heckmann). That device includes two conveyor wheels mounted for rotational movement for conveying containers along either one of a main path of movement for containers to be used later, or a shunt path of movement for containers to be removed and inspected or discarded. The specification of U.S. Pat. Nos. 3,746,165 and 3,727,068 describe bottle inspection machines in which dirty bottles are individually rejected. The bottles, moving in single file, pass an optical inspection unit and when a dirty bottle is detected a double-pronged claw is caused to move at high speed into the path of the bottles so that the flow is stopped and the dirty bottle is captured between the prongs of the claw. A pneumatic ram then gently ejects the dirty bottle in a direction substantially at right angles to the normal flow of bottles. The ram and the claw both retract after the dirty bottle has been rejected thus allowing the bottles upstream to move once more. Other inspection apparatus which utilizes light transmission properties of a bottle in the inspection thereof, and includes means for identifying and removing such defective bottle out from a column or line of like bottles are described in U S. Pat. Nos. 3,349,906; 3,601,616; 3,629,595; 3,746,784; and 3,651,937.

The reliability of the method of discriminating incorporated in the system 11 will depend upon the technique for analyzing the samples as well as the physical properties of the product originally packed in the container. The reliability may be increased by selecting more than one technique (system redundancy) to characterize or "fingerprint" the original product. For example, soft drinks contain emulsions which are susceptible to being characterized by the light scattering methods described above. In addition most soft drinks are sweetened with sucrose or fructose which can be easily detected using commercial indicators.

Figure 5:
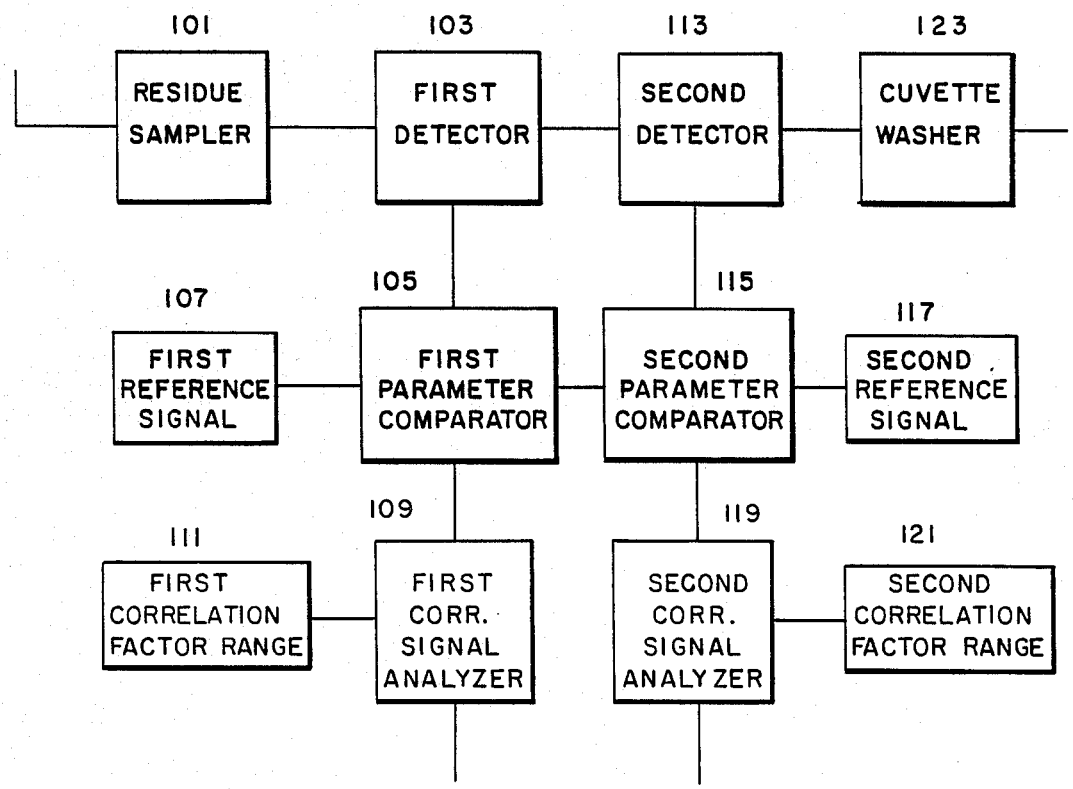
FIG. 5 is a schematic diagram of an alternate embodiment utilizing two or more detector systems.

In FIG. 5 there is illustrated an alternate embodiment for a system for discriminating between contaminated and uncontaminated bottles 100 having a redundancy feature. Samples of the residue of incoming bottles (before washing) are disposed on cuvettes by a residues sampler 101. The cuvette is then transferred to a first detector 103 which utilizes one of the detection technologies previously enumerated. For example the first detector 103 may utilize a transmission measuring device utilizing the differential light scattering technique described above. In that device data (representative of the intensity of light scattered through different angles measured from the incident beam) is generated by the first detector 103. The data is then compared in the first parameter comparator 105 with reference data (first reference signal in FIG. 5) stored in a first memory device 107. The comparison of the data is then analyzed by the first correlator signal analyzer 109 and compared with a correlation factor range stored in a memory device 111. If the response of the residue sample falls within the correlation factor range that has been empirically established for the particular device and the particular product, then the bottle from which the sample was taken is accepted as uncontaminated. If the response of the sample falls outside the range then the bottle is assumed to be contaminated and a reject signal is given. The cuvette is then transported to a second detector 113. The second detector 113 may be for example a sugar analyzer. In such an analyzer a reagent is added to the sample and then examined by a colorimeter. A signal indicative of the intensity of a reference beam transmitted through the sample is then communicated to a second parameter comparator 115. The second parameter comparator compares the detector signal with a second reference signal stored in memory device 117. The two signals are then analyzed by the second correlation signal analyzer 119 using criteria defined in the second correlation factor range stored in memory 121. As with the first detector 103, if the physical response of the residue sample from the second detector 113 falls outside of the correlation factor range then the bottle from which the residue sample was taken is rejected. The cuvettes may be transferred to a cuvette washer 123. Although specific examples are cited in the description of FIG. 5, the detection techniques outlined above may be used in either detector 103 or 113.

While certain of the individual component assemblies of the present invention may be identifiable in the above cited patents none of these references nor any device or combination of components is like that of the present invention, either in arrangement or in the manner of its operation. While specific embodiments of the invention have been shown and described in detail to illustrate the application of the inventive principles, it will be understood that the invention may be embodied otherwise without departing from such principles.

What is claimed is:

1. A method for discriminating between a contaminated container and an uncontaminated container from a population of containers which were once filled with product to be consumed comprising the steps of:
    generating a signal representative of at least one physical response generated by a sample of product residue;
    generating at least one physical response from a sample residue in each container;
    comparing the physical response of the sample residue with the signal representative of the physical response of a product residue; and
    rejecting the container when the physical response of the sample residue does not correlate to the physical response of the product residue, whereby complex analytical systems for detecting a large number of unknown contaminants is avoided by reducing the analytical problem to the detection of known and relatively few products whose presence is used to indicate that the container was not contaminated;

the steps of generating physical responses from product residue and sample residues comprising, directing electromagnetic energy to the residues from a light source, measuring the quality and quantity of electromagnetic energy that interacts with the residues, transmitting signals indicative of the quality and quantity of the electromagnetic energy measured, and collecting color information about the product and sample residues for at least one discrete preselected identification wavelength range within the range of 300 to 700 nanometers.

2. The method of claim 1 wherein the color information from the physical responses of the product and sample residues is generated utilizing from three to eight discrete, preselected identification wavelength ranges.

3. The method of claim 2 wherein the container rejected is in a product filling line.

4. A method for discriminating between a contaminated container and an uncontaminated container from a population of containers which were once filled with product to be consumed comprising the steps of:

generating a signal representative of at least one physical response generated by a sample of product residue;

generating at least one physical response from a sample residue in each container;

comparing the physical response of the sample residue with the signal representative of the physical response of the product; and rejecting the container when the physical response of the sample residue does not correlate to the physical response of the product residue, whereby complex analytical systems for detecting a large number of unknown contaminants is avoided by reducing the analytical problem to the detection of known and relatively few products whose presence is used to indicate that the container was not contaminated;

the steps of generating physical responses from product and sample residues comprising, directing electromagnetic energy to the residues, measuring the quality and quantity of electromagnetic energy that interacts with the product and sample residues, transmitting signals indicative of the quality and quantity of the electromagnetic energy measured, and utilizing gas chromatography to measure the quality and quantity of the electromagnetic energy that interacts with the product and sample residues.

5. The method of claim 4 wherein the presence of a microorganism indicating the presence of product residue is utilized to indicate that the container was not contaminated.

6. The method of claim 5 wherein a sample of a sample residue in a container is extracted from the container and the physical response of the sample residue is generated.

* * * * *